United States Patent [19]

Martin

[11] Patent Number: 5,776,884
[45] Date of Patent: Jul. 7, 1998

[54] CYCLOPENTYLIDENE-CYCLOPENTANOL IN PEREUMERY

[75] Inventor: Angela Martin, Ashford, Great Britain

[73] Assignee: Quest International B.V., Naarden, Netherlands

[21] Appl. No.: 742,843

[22] Filed: Nov. 1, 1996

[30] Foreign Application Priority Data

Nov. 3, 1995 [EP] European Pat. Off. ............ 95307853

[51] Int. Cl.$^6$ .................................................. A61K 7/46
[52] U.S. Cl. ................................................ 512/8; 568/816
[58] Field of Search ................................ 512/8; 568/816

[56] References Cited

U.S. PATENT DOCUMENTS

| 1,965,792 | 7/1934 | Chaux | 512/8 |
| 4,289,658 | 9/1981 | Willis et al. | 512/8 |

FOREIGN PATENT DOCUMENTS

| 0 016 650 | 10/1980 | European Pat. Off. | C07C 49/417 |
| 57-99548 | 6/1982 | Japan | 512/8 |
| WO 81/00845 | 4/1981 | WIPO | C07C 35/21 |

OTHER PUBLICATIONS

Mitsui et al, Bull Chem. Soc. Japan, vol. 39(1) 694–7,1966.

Dang et al, J. Org. Chem., vol. 55, pp. 1432–1438, 1990.

*Primary Examiner*—James H. Reamer
*Attorney, Agent, or Firm*—Pillsbury Madison & Sutro LLP

[57] ABSTRACT

The invention relates to the use of 2-cyclopentylidene-cyclopentanol as fragrance and flavour material. The compound has an indolic odour and is therefore very useful for replacing indole in perfumes and flavourings. Unlike indole it is stable to light and in alkaline media and gives no discolouration.

5 Claims, No Drawings

CYCLOPENTYLIDENE-CYCLOPENTANOL IN PERFUMERY

The present invention relates to the use of 2-cyclopentylidene-cyclopentanol as fragrance and flavour material. It also relates to perfumes and perfumed products as well as flavourings and flavoured products containing this alcohol.

Many synthetic perfume components have been developed, especially in the last decadec to substitute known perfume materials of natural origin. Nevertheless there is a constant need for new synthetic perfume components which are more stable than those previously developed and/or have additional or more delicate odour notes to further complete the fragrance palette from which the perfumer can chose in composing perfumes which are suitable also for various agressive environments. Thus, indole and skatole are well known fragrance materials with a strong animalic odour, often described as faccal. They are extensively used in the art of perfumery, e.g. in various floral perfume compositions, particularly in jamin perfumes and bases. However, indole and skatole suffer from the disadvantage that they are unstable to light and under alkaline conditions, such as in soap, and thus give rise to severe discoloration problems.

2-Cyclopentyl-cyclopentanol is known as a fragrance material under the tradename TELLUROL. It has a minty camphoraceous odour with a slight indolic note. It therefore has various uses in the art of perfumery, but is entirely unsuitable as a replacement for indole or skatole. 2-Cyclopentyl-cyclopentanone is described as useful as a fragrance and flavour material in EP-A-0 016 650. It has a fresh cool minty, menthone-like odour and is especially suitable for dentifrices.

It has now been found that 2-cyclopentylidene-cyclopentanol of the formula below (comprising 2 isomers):

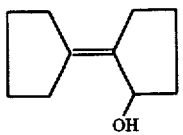

is a valuable fragrance and flavour material with a strong indolic/skatolic odour without any disturbing minty, menthone-like or camphoraceous notes. It is stable to light and in alkaline media and gives no discolouration problems. Thus, in perfumes it is an excellent substitute for indole or skatole and does not show any of the disadvantages of these known fragrance materials. Although the alcohol according to the invention is itself known in the literature, no olfactive properties have been described before.

The compound may be prepared as described in the literature, see: Le Guillanton et al, Bull Soc. Chim. France 1963(3), 611-19; Lamant et al, Compl. rend. 250, 362.4 (1960); Mousseron et al, Bull. Soc. Chim. France 1947, 598-605 and Mitsui et al, Bull. Chem. Soc. Japan 39(1), 694-7 (1966). A particularly useful route starts with the self-aldol condensation of cyclopentanone, followed by reduction of the thus formed 2-cyclopentylidene-cyclopentanone. The reduction may be performed e.g. with a suitable borohydride reducing agent or according to the method of Meerwein, Ponndorf and Verley. These synthesis routes yield mixtures of the isomers and various other minor components. Apart from the usual purification steps such as distillation and/or recrystallization, these mixtures do not require further purification or separation to be used as fragrance materials in the preparation of perfumes. Thus the invention also provides a process for the preparation of a perfume comprising the steps of reducing 2-cyclopentylidene-cyclopentanone, purifying the reaction mixture and combining the purified reaction mixture with other fragrance materials.

Thus, the alcohol according to the invention may be used as such to give indole/skatole-like odour or flavour notes to all sorts of products. More particularly, it may be usefully incorporated in perfumes and flavourings. For the purpose of this invention a perfume is defined as a mixture of various fragrance materials, if desired dissolved in a suitable solvent or mixed with a solid substrate, which is used to provide a desired odour to the skin or to all sorts of products. Examples of such perfumed products are: fabric washing powders and liquids, fabric softeners and other fabric care products; detergents, hard surface cleaners and household cleaning, scouring and disinfection products; air fresheners, room sprays and pomanders; candles; soaps, shampoos, hair conditioners, bath and shower gels and other personal care products; cosmetics such as creams, ointments, toilet waters, preshave-, aftershave- and other lotions, talcum powders, body deodorants and antiperspirants.

Known fragrance and flavour materials which may be advantageously combined with the alcohol according to the invention may be natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds. Such materials are mentioned, for example, in S. Arctander, Perfume and Flavor Chemicals (Montclair, N.J., 1969), in S. Arctander, Perfume and Flavor Materials of Natural Origin (Elizabeth, N.J., 1960), in "Flavor and Fragrance Materials—1991", Allured Publishing Co. Wheaton, Ill. USA and in Fenaroli's Handbook of Flavor Ingredients, Vol I & II. CRC Press, Boca Raton 1995.

Examples of fragrance materials which can be used in combination with the esters according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert-butyl cyclohexyl acetate, isononyl acetate, vetiveryl acetate, vetiverol, α-hexylcinnamaldehyde, 2-methyl-3-(p-tert-butyl-phenyl) propanal, 2-methyl-3-(p-isopropylphenyl)propanal, 3-(p-tert-butylphenyl)-propanal, tricyclodecanyl acetate, tricyclodecenyl propionate, 4-(4-hydroxy-4 methyl-pentyl)-3-cyclohexenecarbaldehyde, 4-(4-methyl-3-pentenyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl ioobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethyl-ionones, irones, cis-3-hexanol and esters thereof, indan musks tetralin musks isochroman musks macrocyclic ketones, macrolactone musks ethylene brassylate, aromatic nitromusks.

Solvents which can be used in perfume compositions which contain compounds according to the invention are, for example: ethanol, isopropanol, diethylene glycol monoethyl ether, dipropylene, glycol, diethyl phthalate, triethyl citrate, etc.

The amounts in which the alcohol according to the invention can be effectively used in perfumes or flavourings, or products to be perfumed or flavoured, may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the person skilled in the art to be able to use the alcohol according to the invention for his specific purpose. In perfumes an amount of 0.01% by weight or more of the alcohol according to the invention will generally have a clearly perceptible olfactive effect. Preferably the amount is 0.05% by weight, but due to the odour character of the compound it will seldom be more than 10% by weight. The amount of the alcohol according to the invention present in products will generally be at least 1 ppm by weight.

The following examples are only intended to illustrate the preparation and use of the alcohol according to the invention, but the invention is not in any way limited thereto.

EXAMPLE 1

Preparation of 2-cyclopentylidene-cyclopentanol
A 2-Cyclopentylidene-cyclopentanone.

A 2 liter round bottom flask, fitted with a mechanical stirrer, a reflux condenser and a thermometer, was charged with 951 g (11.3 mol) of cyclopentanone and a solution of 38.2 g of potassium hydroxide in 250 ml of water. The mixture was heated with stirring at about 100° C. for 5 hours. After cooling to room temperature 200 ml of diethyl ether was added and the aqueous and organic phases were separated. The organic phase was washed twice with 200 ml of water, once with 200 ml of 10% aqueous HCl solution and twice with 200 ml of saturated brine solution. The organic phase was dried over anhydrous magnesium sulphate. After filtration of the organic liquid, the solvent was removed using a rotary evaporator and 813.5 g of crude product was obtained. This was fractionated under reduced pressure (0.2–0.3 kPa). The desired product distilled at 105°–108° C. and was obtained in 73% yield (623 g).

B 2-cyclopentylidene-cyclopentanol

A 2 liter round bottom flask, fitted with a mechanical stirrer, a reflux condenser and a thermometer, was charged with 412.4 g (2.75 mol) of 2-Cyclopentylidene-cyclopentanone and 500 ml methanol. The mixture was stirred until homogeneous at room temperature and then 40 g of sodium borohydride was added in small portions over a period of 1.5 hour. The reaction mixture was thereafter stirred for another 4 hours. During addition as well as thereafter the temperature was kept below 40° C. by cooling with a cold water bath if necessary. The reaction mixture was further stirred overnight. Thereafter it was quenched by dropwise addition, with stirring, of 250 ml of water. The aqueous and organic layers were separated and the aqueous layer extracted twice with 200 ml diethyl ether. The combined organic layers were washed with 200 ml water and dried over magnesium sulphate. After filtration the solvent was removed using a rotary evaporator and 444 g of crude product were obtained. This was fractioned under reduced pressure (0.4 kPa) through a 0.5 meter Sulzer-packed column. Fractions were collected at 90°–100° C. and odour assessed. The total of fractions with an acceptable odour was 182.9 g. The product could be further purified by recristallization from methanol.

EXAMPLE 2

A perfume compostion of the "White Lilac" type was prepared according to the following recipe:

| | |
|---|---|
| Phenylethylalcohol | 35.2% w/w |
| Hydroxycitronellal | 32.0 |
| Cinnamic Alcohol | 17.5 |
| Styrax Resinoid | 7.0 |
| Anisic Aldehyde | 4.4 |
| Jasmin Absolute | 3.5 |
| 2-Cyclopentylidene-cyclopentanol | 0.4 |
| Total | 100% |

EXAMPLE 3

A perfume compostion of the "Orange Flower" type was prepared according to the following recipe:

| | |
|---|---|
| Phenylethylalcohol | 21.0% w/w |
| Linalool | 21.0 |
| Petitgrain Oil | 17.0 |
| Methyl Anthranilate | 13.0 |
| Nerol 97% | 12.0 |
| Benzyl Acetate | 8.0 |
| Aurantion (Q) | 4.0 |
| Orange Flower Absolute | 2.0 |
| Aldehyde C10 (10% in diethylphthalate) | 0.8 |
| Geranyl Formate | 0.6 |
| Aldehyde C8 (10% in diethylphthalate) | 0.4 |
| 2-Cyclopentylidene-cyclopentanol | 0.2 |
| Total | 100% |

(Q) marketed by Quest International

I claim:

1. A perfume comprising known fragrance materials together with an effective amount of 2-cyclopentylidene-cyclopentanol.

2. A perfume according to claim 1 containing at least 0.01% by weight of 2-cyclopentylidene-cyclopentanol.

3. A perfume product comprising an effective amount of 2-cyclopentylidene-cyclopentanol.

4. A perfume product according to claim 3 containing at least 1 ppm by weight of 2-cyclopentylidene-cyclopentanol.

5. A perfume free of indole and skatole, said perfume comprising an amount of 2-cyclopentylidene-cyclopentanol effective to provide an indolic or skatolic odor.

* * * * *